US010582752B2

(12) United States Patent
Ho et al.

(10) Patent No.: US 10,582,752 B2
(45) Date of Patent: Mar. 10, 2020

(54) NIPPER DEVICE WITH MAGNETIZED HANDLE

(71) Applicant: MEGATOOL, INC., Santa Ana, CA (US)

(72) Inventors: Peter Phuc Ho, Westminster, CA (US); Tammy Tran, Santa Ana, CA (US); Elvis Ho, Santa Ana, CA (US)

(73) Assignee: MEGATOOL, INC., Santa Ana, CA (US)

( * ) Notice: Subject to any disclaimer, the term of this patent is extended or adjusted under 35 U.S.C. 154(b) by 0 days.

(21) Appl. No.: 15/453,837

(22) Filed: Mar. 8, 2017

(65) Prior Publication Data

US 2017/0258199 A1    Sep. 14, 2017

Related U.S. Application Data

(60) Provisional application No. 62/307,299, filed on Mar. 11, 2016.

(51) Int. Cl.
*A45D 29/02* (2006.01)
*A61N 2/06* (2006.01)
*B25G 1/10* (2006.01)

(52) U.S. Cl.
CPC ............ *A45D 29/02* (2013.01); *A61N 2/06* (2013.01); *B25G 1/102* (2013.01); *A45D 2029/026* (2013.01)

(58) Field of Classification Search
CPC .... A45D 2029/026; A45D 29/02; A61N 2/06; B25G 1/102
USPC .......................................................... 30/28
See application file for complete search history.

(56) References Cited

U.S. PATENT DOCUMENTS

| | | | | |
|---|---|---|---|---|
| 5,139,014 | A * | 8/1992 | Chang | A61H 7/001 601/118 |
| 5,214,854 | A * | 6/1993 | Mennicken | B25B 7/18 30/186 |
| 5,382,222 | A * | 1/1995 | Yih-Jong | A61H 7/003 601/135 |
| 5,795,242 | A | 8/1998 | Ree | |
| 5,987,752 | A | 11/1999 | Swanstrom, Jr. | |
| 6,076,264 | A | 6/2000 | Meckel | |
| 6,344,021 | B1 | 2/2002 | Juster et al. | |
| 6,398,712 | B1 | 6/2002 | Hendricksen | |
| 7,210,230 | B2 | 5/2007 | Wurzel | |
| 7,536,791 | B2 | 5/2009 | Toyama | |
| 8,226,540 | B1 | 7/2012 | Chi | |
| 8,505,420 | B2 * | 8/2013 | Alfaro | B25G 1/10 206/350 |
| 8,740,764 | B1 | 6/2014 | Newman | |
| 2003/0163896 | A1 | 9/2003 | Rabello | |

(Continued)

OTHER PUBLICATIONS

Authorized Officer Thomas, Shane, "The International Search Report and the Written Opinion of the International Searching Authority, or the Declaration" dated Jun. 1, 2017. PCT/US17/21666. 9 Pages.

*Primary Examiner* — Hwei-Siu C Payer
(74) *Attorney, Agent, or Firm* — Stetina Brunda Garred and Brucker (57) ABSTRACT

A nipper device that is useful in the care and grooming of nails of the hands and feet. The nipper device provides cutting blades where are sharper, more durable, and more hygienic. The handles of the device may be magnetized to provide magnetic therapy benefits to a user of the device.

21 Claims, 4 Drawing Sheets

(56) References Cited

U.S. PATENT DOCUMENTS

| | | | |
|---|---|---|---|
| 2004/0088824 A1* | 5/2004 | Hsien | B25G 1/00 16/111.1 |
| 2005/0217118 A1 | 10/2005 | Mah | |
| 2008/0271324 A1 | 11/2008 | Fryer | |
| 2009/0078278 A1 | 3/2009 | Tran | |
| 2012/0000325 A1* | 1/2012 | Hsieh | B25B 15/02 81/185.2 |
| 2012/0011723 A1 | 1/2012 | Flaten | |
| 2017/0258199 A1* | 9/2017 | Ho | A45D 29/02 |

* cited by examiner

NIPPER DEVICE WITH MAGNETIZED HANDLE

CROSS-REFERENCE TO RELATED APPLICATIONS

This application claims the benefit of U.S. Provisional Application Ser. No. 62/307,299, filed Mar. 11, 2016, the contents of which are expressly incorporated herein by reference.

STATEMENT RE: FEDERALLY SPONSORED RESEARCH/DEVELOPMENT

Not Applicable

BACKGROUND

A. Technical Field

This disclosure relates to nipper devices for use during manicures and pedicures. More specifically, this disclosure relates to a nipper device with Tungsten Carbide cutting jaws and magnetized handles.

B. Description of the Related Art

Nipper devices which are typically constructed of durable stainless steel, are used by commercial spas, salons, and other commercial ventures which offer manicures and pedicures are well known. These nipper devices need to stand up to commercial use, and thus must be durable and effective for their intended purpose. Nipper devices typically include a pair of opposed handles and a pair of opposed blades, and are configured such that by squeezing the handles, the blades are moved to cut a finger nail or toe nail. When used in a spa, salon or other commercial venture, the nipper device is typically operated by an esthetician or other care specialist, and is used to cut the finger nails or toe nails of a customer.

The conventional design of nipper devices has been primarily focused on improving the effects of the nipper device for the customer, i.e., the person whose nails are being cut. However, what is less recognized in conventional nipper device design is the use of the device by the operator of the tool. In this regard, conventional nipper device design suffers from several deficiencies, particularly when viewed from the perspective of the individual operating the nipper device.

For instance, the repetitive motion of the nipper device, particularly when used repeatedly in a professional setting, may lead to injury. Repetitive motion injuries are well documented in other endeavors, including sports such as running and golf, and types of work, such as carpentry and office work which requires continuous or nearly continuous typing on a keyboard. However, the potential for such injuries is less recognized in nail care. Nail care specialists, in addition to clipping nails using a nipper device, may also be required to operate other hand-held devices, such as brushes, nail files, and mandrels. The nail care providers also use their hands for the massaging of hands and feet. The foregoing manual activities of the nail care specialist increase the likelihood of fatigue and potential injury.

Furthermore, another deficiency associated with conventional nipper devices is that the blades on the nipper device may become dull over time. When the blades become dull, the nipper device may become more dangerous to use, as the operator of the tool may be required to squeeze the handles with more force to cut the nail. The additional force may lead to an inadvertent loss of control of the nipper device, which may cause injury to the customer and/or the operator of the nipper device. Therefore, when the blades become dull, the blades may require sharpening, which may be time consuming, and thus, undesirable to the operator of the nipper device.

Accordingly, there is a need in the art for a nipper device which is safe and easy to use, and which also provides therapeutic benefits to the individual operating the tool. Various aspects of the present disclosure are directed to this need, as will be discussed in more detail below.

BRIEF SUMMARY

According to one embodiment, there is provided a nipper device, including a jaw with a first blade and a second blade, a pivot section, including a lower pivot portion including a first aperture therethrough, an upper pivot portion including a second aperture therethrough. The nipper device further includes a pin and a handle section, with a first handle, a second handle with an attachment point. A spring, which has a straight end and a curved end, is attached to the second handle at an attachment point with a retention element. The first aperture and second aperture combine to form a continuous bore with the pin resting therein. At least a portion of the first blade and the second blade are made from tungsten carbide. The curved end of the spring rests against the first handle.

According to another aspect of the present disclosure, there is provided a nipper comprising a jaw including a first blade and a second blade pivotable relative to the first blade, with the jaw being formed from a carbide material. The nipper further includes a handle coupled to the jaw. The handle includes a first arm coupled to the first blade and a second arm coupled to the second blade, with the first arm being pivotable relative to the second arm. The jaw and handle are configured such that pivotable movement of the first arm relative to the second arm causes pivotal movement of the first blade relative to the second blade. The first and second arm are magnetized so as to emit a magnetic force therefrom.

The nipper may additionally include at least one first magnet coupled to the first arm. The at least one first magnet may include a plurality of first magnets coupled to the first arm. The first arm may include a plurality of recesses formed therein, with the plurality of first magnets being located in respective ones of the plurality of recesses. The at least one first magnet may comprise a sleeve extending over at least a portion of the first arm. The nipper may additionally include at least one second magnet coupled to the second arm.

The nipper may include a spring operatively engaged to the first arm and the second arm, with the spring being adapted to impart a biasing force on the first arm and the second arm which urges the first arm and the second arm to pivot away from each other.

The nipper may comprise a pivot pin coupled to the first arm and the second arm, with the first arm and the second arm being pivotable about the pivot pin.

The first blade and the second blade may include respective linear blade edges.

According to another embodiment, there is provided a nipper comprising a cutting portion including a first cutting edge and a second cutting edge, with the first and second cutting edges being pivotable relative to each other to effectuate cutting of an object. The nipper further includes a handle portion coupled to the cutting portion. The handle portion includes a pair of handle arms coupled to respective ones of the first cutting edge and the second cutting edge, with the pair of handle arms being pivotable relative to each other. The nipper additionally comprises a plurality of magnetized massaging elements. Each massaging element is coupled to a respective handle arm to and configured to emit a magnetic field and provide a massaging effect on a user gripping the handle portion.

According to yet another embodiment, there is provided a method of forming a nipper. The method includes forming a pair of nipper arms. Each nipper arm has a cutting portion and a handle portion, with the cutting portion being at least partially comprised of a carbide material. The method further includes magnetizing the handle portion, and connecting the pair of nipper arms such that the pair of nipper arms are pivotally connected to each other.

The forming step may include brazing each nipper arm to join the carbide material to the corresponding handle portion.

The magnetizing step may include connecting at least one magnet to each nipper arm. The step of connecting at least one magnet to each nipper arm may include placing each magnet in a corresponding recess formed in the nipper arm.

The connecting step may include connecting the pair of nipper arms via a pivot pin.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Embodiments of the disclosed device provide a tool useful in care and grooming of nails of the hands and feet. The detailed description set forth below in connection with the appended drawings is intended as a description of aspects of the presently preferred embodiments of the nipper device is not intended to represent the only forms in which the present disclosure may be constructed or utilized. It is to be understood, however, that the same or equivalent functions and structures may be accomplished by different embodiments that are also intended to be encompassed within the spirit and scope of the disclosure. As denoted elsewhere herein, like element numbers are intended to indicate like or similar elements or features.

Figure 1:
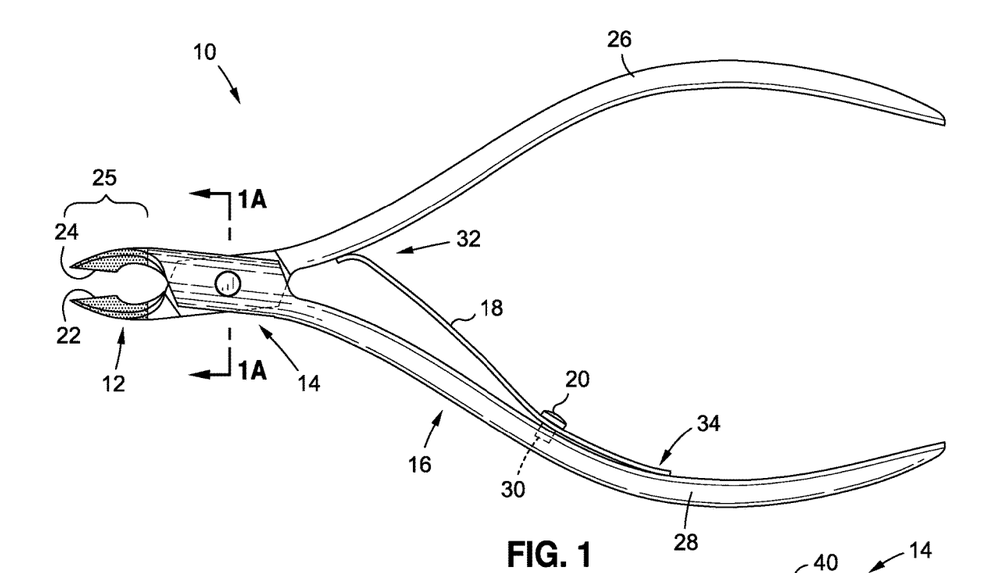
FIG. 1 shows a top view of a first embodiment of a nipper device.

FIG. 1 shows a top view of the nipper device 10 constructed in accordance with an embodiment of the present disclosure, with the nipper device 10 being adapted for use as a grooming tool for the nails of a user's hands and/or feet. In general, the nipper device 10 includes a jaw 12, a pivot section 14, and a handle section 16. As will be discussed in more detail below, the jaw 12 is preferably formed of a Carbide material, thereby allowing the jaw 12 to be sharp and easy to use. The Carbide material is also recyclable, and thus, the nipper device 10 is environmentally friendly. Furthermore, the handle section 16 may be specifically configured and adapted to be magnetized to provide a therapeutic benefit to a user, and may also enhance the grippability thereof.

In more detail, the jaw 12 includes a first blade 22 and an opposing second blade 24 pivotable relative to the first blade 22. The first and second blades 22, 24 include respective linear blade edges, which pivotally reciprocate relative to each other to effectuate trimming of a nail on a hand and/or a foot.

The handle section 16 includes a first handle 26, a second handle 28, a spring 18, and a retention element 20. According to one embodiment, the first handle 26 is a continuous extension of the first blade 22, while the second handle 28 is a continuous extension of the second blade 24. Each handle 26, 28 includes an arcuate section to facilitate gripping of the handle section 16. The first and second handles 26, 28 are pivotally coupled to each other, and are pivotable between a first position and a second position. The first position is shown in FIG. 1, and corresponds to the first and second blades 22, 24 being spaced apart from each other. The first and second handles 26, 28 are moved toward each other as they transition from the first position to the second position, with the second position being associated with the first and second blades 22, 24 in contact with each other. Thus, the handles 26, 28 and blades 22, 24 are configured such that as the handles 26, 28 are moved toward each other, the blades 22, 24 are also moved toward each other, and conversely, as the handles 26, 28 are moved away from each other, the blades 22, 24 are also moved away from each other. The spring 18 is in operative communication with the first and second handles 26, 28 and applies a biasing force on the handles 26, 28 which biases the handles 26, 28 toward the first position.

As noted above, the nipper device 10 of FIG. 1 is in the first, or ready, position. The spring 18 is attached by the retention element 20 to the second handle 28. When attached, a portion of the spring 18 is spaced apart from the second handle 28. A first end 32 of the spring 18 is slightly curved and biases against the first handle 26. A second, or opposite end 34 of the spring 18 is straight and biases against the second handle 28. The biasing of the spring 18 urges the handles 26, 28 toward the first position, and thus, the first blade 22 and the second blade 24 are in an open or spaced-apart position. To transition the handles 26, 28 from the first position toward the second position, the biasing force of the spring 18 is overcome by the gripping force applied by a user's hand. One of ordinary skill in the art will readily recognize that the positioning of the attachment point 30, spring 18 and retention element 20 may be reversed. That is, the attachment point may be on the first handle 26, with the curved end of the spring 18 biasing against the second handle 28.

Figures 1A, 2:
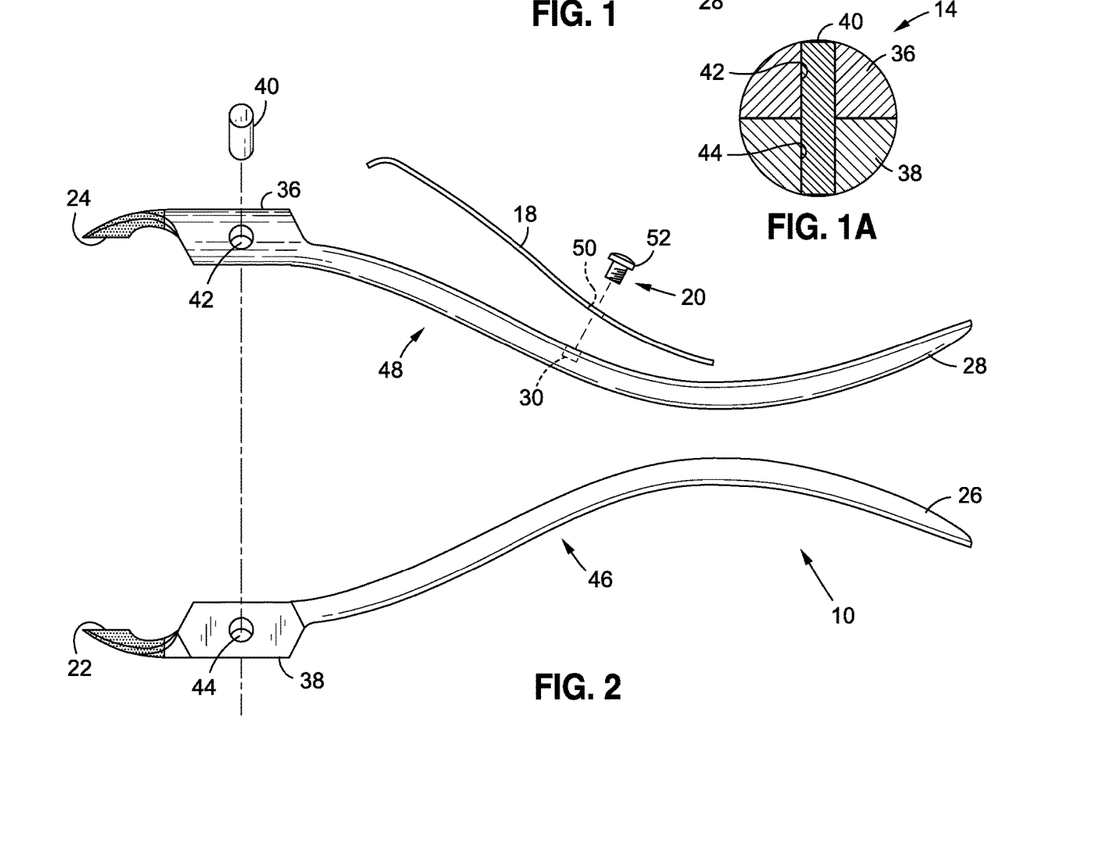
FIG. 1A shows a cross section view a pivot joint of the nipper device.
FIG. 2 shows an exploded view of the nipper device.

FIG. 1A shows a cross section view of the pivot section 14 on a plane indicated by the line 1A-1A in FIG. 1. Shown are a pivot section upper pivot portion 36 extending between the second blade 24 and the second handle 28, a pivot section lower pivot portion 38 extending between the first blade 22 and the first handle 26, and a pin 40. The upper pivot portion 36 and lower pivot portion 38 include generally flat inner surfaces that reside against one another, while also including respective, arcuate or curved outer surfaces. A first aperture 44 is formed through the lower pivot portion 38 and a second aperture 42 is formed through the upper pivot portion 36. The first aperture 44 and the second aperture 42 are correspondingly aligned to form a common bore. The pin 40, around which the upper pivot portion and the lower pivot portion rotate, rests in the bore. In this regard, the pin 40 defines a pivot axis about which the blades 22, 24 and handles 26, 28 pivot.

FIG. 2 shows an exploded view of the nipper device 10. In the exemplary embodiment, the first blade 22, lower pivot portion 38, and first handle 26 form a first integrated piece 46 (i.e., a first arm), while the second blade 24, upper pivot portion 36, and second handle 28 form a second integrated piece 48 (i.e., a second arm). In this embodiment, the portion of the first blade 22 and the second blade 24 indicated by the bracket 25 are entirely made from Tungsten Carbide, and are brazed to the lower pivot portion 38 and upper pivot portions 36, respectively. The Tungsten Carbide material is represented throughout the Figures as a shaded region of the nipper device. The Carbide material allows the blades 22, 24 to maintain their sharpness, and thus, the nipper device 10 may have a longer lifespan than conventional stainless steel blades. Furthermore, the enhanced sharpness of the blades 22, 24 allows the operator of the nipper device 10 to effectuate the cutting of a finger nail or toe nail with minimal effort, which mitigates inadvertent mistakes and enhances overall safety to the operator of the device 10, as well as the customer. The enhanced sharpness also allows for quicker manicuring of finger nails or toe nails, and thus, the nipper device 10 may be more profitable for salons, as less time may be required for each customer. The Carbide tip 12 may also provide a visual aid for the individual using the nipper device 10, since the Carbide material may visually contrast with the material (e.g., stainless steel) used to form the remainder of the nipper device 10. Thus, the visual aid may allow the individual to quickly and easily align the tip 12 with the nail that is to be cut. The Carbide portion is also recyclable, and thus, provides environmental benefits over non-recyclable materials. Given the relatively high cost of the Carbide material relative to other commonly used materials, such as stainless steel, it is contemplated that the Carbide material from an old nipper device may be re-used when making a new nipper device.

As noted above, the Carbide portions of the blades 22, 24 may be brazed to the lower and upper pivot portions, 38, 36, respectively. Brazing is a metal-joining process in which two or more metal items are joined together by melting and flowing a filler metal into the joint, the filler metal having a lower melting point than the adjoining metal. Typical filler metals which work well for brazing tungsten carbide to stainless steel have a melting point around 645 degrees Celsius. Brazing differs from welding in that it does not involve melting the work pieces and from soldering in using higher temperatures for a similar process, while also requiring much more closely fitted parts than when soldering. The filler metal flows into the gap between close-fitting parts by capillary action. The filler metal is brought slightly above its melting (liquid) temperature while protected by a suitable atmosphere, usually a flux. It then flows over the base metal (known as wetting) and is then cooled to join the work pieces together. It is similar to soldering, except the temperatures used to melt the filler metal are typically higher for brazing. A major advantage of brazing is the ability to join the same or different metals with considerable strength.

Although the bracketed portion 25 of the blades 22, 24 shown in FIGS. 1 and 2 are formed from Tungsten Carbide, in other embodiments only a smaller portion of the first and second blades 22, 24 may be made from Tungsten Carbide, for example only the cutting edge of the blades 22, 24 may be made from Tungsten Carbide. In other embodiments, the entirety of the first and second blades 22, 24 may be made from Tungsten Carbide.

Tungsten Carbide is an extremely durable material. Tungsten Carbide is also a relatively expensive material when compared with other relatively durable materials that are acceptable for even medical use, such as stainless steel. Thus, making a portion of a tool that requires sharpness, durability, and does not harbor bacteria offers a blend of performance and cost, when contrasted with the expense of making an entire tool from tungsten carbide.

Beyond durability, Tungsten Carbide provides additional advantages over stainless steel. The Tungsten Carbide matrix is much more dense, and thus necessarily less porous than the stainless steel alloy. Thus, not only is it more durable, capable of holding a sharp edge for longer periods of time, but due to its low porosity, it is also much less likely to harbor bacteria or to rust. This property means that the tool may be sanitized and sharpened less often, and thus is more available for use. It also is more hygienic, as the anti-bacterial nature of the lower porosity means that the tool is less likely to cause infection in a client. Tungsten Carbide may also be recycled, and thus, as noted above, provides an environmental benefit. In this regard, a first portion of the nipper device may be formed of a first recyclable material (e.g., Tungsten Carbide), while a second portion of the device may be formed from a second recyclable material (e.g., stainless steel).

Although a preferred material for the blades 22, 24 is Tungsten Carbide, those skilled in the art will readily appreciate that the scope of the present disclosure is not limited thereto. Indeed, other materials known by those skilled in the art may also be used.

It is contemplated that the lower pivot portion 38 and first handle 26 are cast, stamped, molded or forged as a single piece and are made from stainless steel, or any material suitable for brazing to attach the first blade 22. Likewise, the upper pivot portion 36 and second handle 28 are cast, molded, stamped, or forged as a single piece and are made from stainless steel, or any material suitable for brazing to attach the second blade 24. In other embodiments, the lower pivot portion 38 and first handle 26, and the upper pivot portion 36 and the second handle 28 may be made from separate pieces and assembled to form an integrated piece. In still other embodiments, the first blade 22 is attached to the lower pivot portion 38 and the second blade 24 is attached to the upper pivot portion 36 by welding, or via an adhesive, or any method or device known in the art which provides sufficient durability for long term commercial use of the nipper device 10.

One skilled in the art will recognize that the pieces of the pivot section 14 may be reversed, such that the upper pivot portion may be attached to the first blade and the first handle, and the lower pivot portion may be attached to the second blade and the second handle.

As discussed in reference to FIG. 1A, and as shown by the dashed line in FIG. 2, the first aperture 44 is formed through the lower pivot portion 38 and the second aperture 42 is formed through the upper pivot portion 36. The first aperture 44 and the second aperture 42 are correspondingly aligned to form a common bore. The pin 40, which has an outer circumference smaller than an inner circumference of the common bore, rests in the common bore.

FIG. 2 also depicts an exemplary attachment of the spring 18 to the second handle 28. In particular, the retention element 20 used to connect the spring 18 to the second handle 28 passes through an opening 50 in the spring 18. The opening outer diameter is less than the outer diameter of a head 52 on one end of the retention element 20, and thus, when the retention element 20 is secured to the second handle 28, the retention element 20 holds the spring 18 in place, attaching it to the second handle 28 at the attachment point 30. In the embodiment shown in FIG. 2, the attachment point 30 is a recess in the second handle 28. The recess is threaded to accommodate a threaded retention element 20. However, in other embodiments, the attachment point is not a recess but simply a point at which the retention element 20 attaches. The retention element 20, when surface mounted, may be welded or attached with an adhesive, or any method secure enough to withstand commercial use of the nipper device 10. In other embodiments the attachment point 30 may be recessed, but not threaded, in order to add more stability to the retention element 20, which also is not threaded, and may be welded into the recess or attached with an adhesive, or any method of attachment which will withstand commercial use of the nipper device 10.

Figure 3:
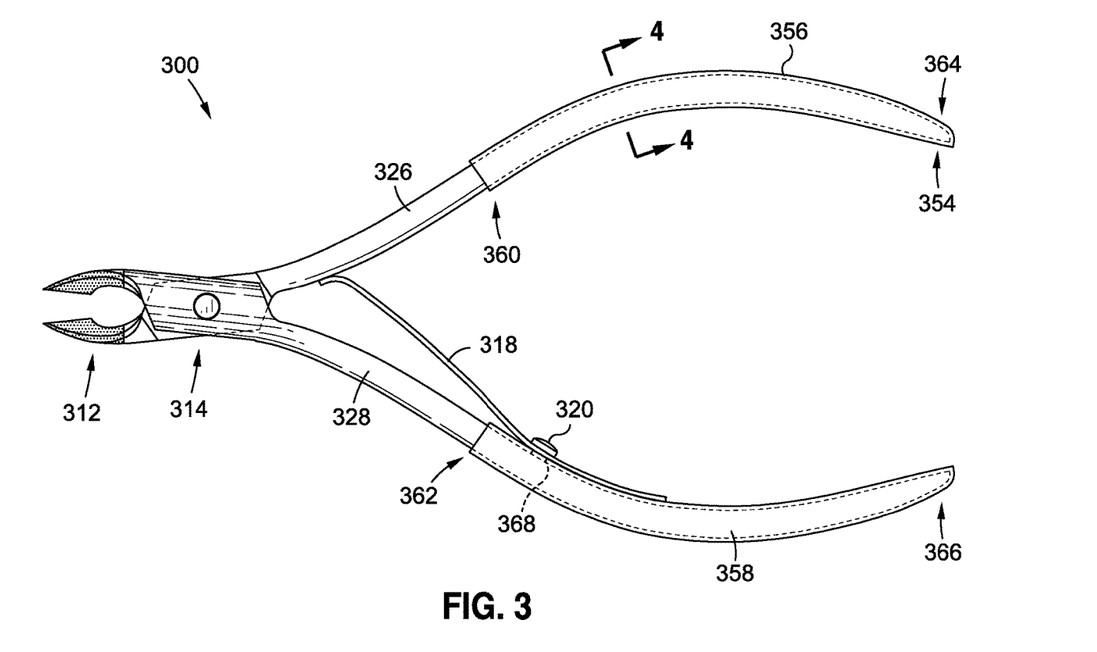
FIG. 3 shows a top view of an alternative embodiment of the nipper device.

FIG. 3 shows an alternative embodiment of the nipper device 300. In this embodiment, both the first handle 326 and the second handle 328 are magnetized. From a first end 354 of the first handle 326 opposite the jaw 312, the magnetization extends along the length of the handle 326 and terminates at a point short of the pivot section 314. According to one embodiment, the magnetization should terminate at a distance sufficiently spaced from the pivot section 314 so that the magnetization does not interfere with the operation of the nipper device 300. The magnetization of the second handle 328 mirrors that of the first handle 326. Further, the magnetic fields generated by the magnetization of the first handle 326 and the second handle 328 do not interact in a way counterproductive to the biasing of the first handle 326 and the second handle 328 caused by the spring 318.

In this embodiment, the first handle 326 and the second handle 328 are magnetized by placing a first sleeve 356 of magnetic material over the first handle 326 and a second sleeve 358 of magnetic material over the second handle 328. The first sleeve 356 of magnetic material and the second sleeve 358 of magnetic material have respective open ends 360, 362 and respective closed ends 364, 366. The sleeves 356, 358 slide over their respective handle 326, 328 until the handle end opposite the jaw 312 comes into contact with the closed end of the sleeve 356, 358. Because of the closed end of the sleeve 356, 358 of magnetic material, the portion of the first handle 326 and the second handle 328 which is magnetized may be controlled by the length of the sleeve 356, 358 of magnetic material. The length of the first sleeve 356 of magnetic material and the second sleeve 358 of magnetic material will partly determine where the location of the magnetic field produced by each sleeve 356, 358 in relation to the first and second handles 326, 328. The exact magnet material chosen and the amount of that material in the sleeves 356, 358 will also affect the strength, and thus, the location of the magnetic field. Ideally, the magnetic field will cover the entirety of the area a user will likely grip the handles 326, 328, thus maximizing magnetic therapy benefits. Further, proper positioning of the sleeves 356, 358 and controlling the magnetic field generated by controlling the amount of magnetic material and magnetization of the magnetic material of the sleeves 356, 358 will serve to prevent interference with the operation of the pivot section 314 or the biasing of the spring 318.

It is recognized that the magnetic field associated with the magnetic material provides several therapeutic benefits to the individual gripping the nipper device 300. For instance, the magnetic field may increase the flow of blood. It is also believed that the magnetic field may improve the functioning of the automatic nervous system, which may also stimulate blood flow to the affected area. Magnetic therapy may also diminish pain, particularly arthritic pain. Thus, for a manually operated tool, the ability to diminish arthritic pain may be particularly advantageous. Magnetic therapy is also believed to improve one's ability to heal from injury. For more information regarding magnetic therapy, please refer to U.S. Pat. No. 6,344,021, entitled Magnetic Therapy Patch, the contents of which are expressly incorporated herein by reference.

By incorporating the magnets into the handle of the nipper device 300, the magnets are available to the user upon use of the device 300. Magnets incorporated in the handle have advantages over other therapeutic magnet devices, which can interfere with the manual activities commonly associated with nail care.

In addition to therapeutic benefits, the magnets incorporated into the nipper device 300 may provide utilitarian benefits. For instance, the magnets may allow the nipper device 300 to be stored on an outer surface of a metallic structure, such as a counter, wall, cabinet, etc. Thus, the nipper device 300 may be conveniently stored on the outer surface of the metallic structure, and easily accessed when needed.

In the embodiment depicted in FIG. 3, the second sleeve 358 of magnetic material covering the second handle 328 has a cutout 368 in the sleeve to accommodate the passage of the retention element 320 through the sleeve 358 and attaching the retention element 320 to the second handle 328.

The same style of magnetic sleeve used in this embodiment may be retrofitted to prior art nipper devices in order to magnetize the handles. In addition to the added benefits of magnetic therapy provided by the sleeves, the sleeves may also provide a further benefit of increased friction and therefore, ease of grip for a user.

Figure 4:
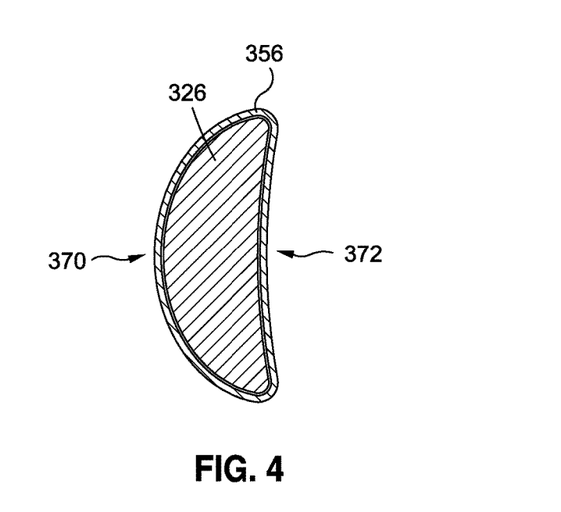
FIG. 4 shows a cross section of the handle of the embodiment of FIG. 3.

FIG. 4 shows a cross section of handle 326 of the nipper device 300 on a plane indicated by the line 4-4 in FIG. 3. The handle 326 has a cross section with a curved or arcuate exterior portion 370 and a relatively flat interior portion 372. The curved exterior portion 370 provides an easier grip for a user. The sleeve 356 of magnetic material may be of any shape and magnetic material which is malleable enough to conform to the cross section of the handle once the sleeve 356 of magnetic material is place over the handle 326. In other embodiments, the nipper device might have handle cross sections which are more crescent shaped, or round, or with the exterior surface varied or textured, such that a user's grip may be improved or less material may be used or both.

Figure 5:
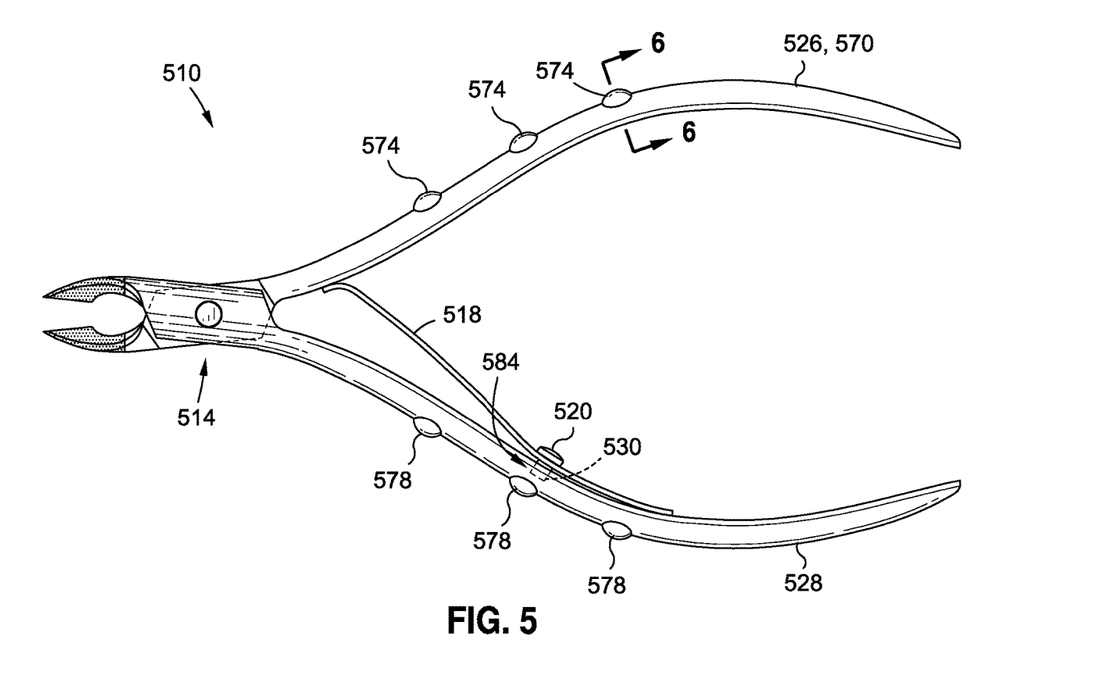
FIG. 5 shows a top view of another alternative embodiment of the nipper device.

FIG. 5 shows another alternative embodiment of the nipper device 510, with the first handle 526 and the second handle 528 being magnetized. In this embodiment, the magnetization is achieved by surface mounting, or mounting in a corresponding recess, a first plurality of magnetized slugs 574 to the first handle 526 and surface mounting, or mounting in a corresponding recess, a second plurality of magnetized slugs 578 to the second handle 528. When surface mounted, the magnetized slugs may be attached by welding, adhesives, or any method capable of durably attaching the slugs to the first handle 526 and the second handle 528 such that the slugs remain in place on the corresponding handle 526, 528. Similar to the previous embodiment, relative to the pivot section 514, the adjacent one of the first plurality of magnetized slugs 574 on the first handle 526 and the adjacent one of the second plurality of magnetized slugs 578 on the second handle 528 are positioned on their respective handles 526, 528 sufficiently far from the pivot section 514 so as not to interfere with the operation of the pivot section 514. The first and second plurality of slugs 574, 578 are also placed along the first and second handle 526, 528, respectively, such that they do not interfere with the biasing of the spring 518. In other embodiments, all of the magnetized slugs may be mounted in recesses in the handles, or all may be surface mounted. Recess mounted slugs 574, 578 will be discussed in further detail below.

Portions of the magnetized slugs 574, 578 extending beyond the outer surface 570 of the first handle 526 and the outer surface of the second handle 528 are rounded off to a domed shape. This shape aids the user in gripping the respective handle 526, 528, as well as improving comfort for the user gripping the handle 526, 528. The user may be further aided in gripping the first handle 526 and the second handle 528 by the spacing of the magnetized slugs 574, 578 on the handle 526, 528. The slugs 574, 578 may be evenly spaced or variably spaced along the respective handle 526, 528, or a combination of some evenly spaced slugs 574, 578 with some variably spaced slugs 574, 578.

As further shown, a magnetized slug 578 is positioned on the second handle 528 adjacent a recessed attachment point 530. The recess for mounting the magnetized slug 578, and the recessed attachment point 530 terminate at a common end 584. The magnetized slug 578 is positioned to correspond with the recessed attachment point 530 performs the dual purpose of helping retain the retention element 520 in the recess, and to provide magnetic therapy effects for the user of the nipper device 510.

Figure 6:
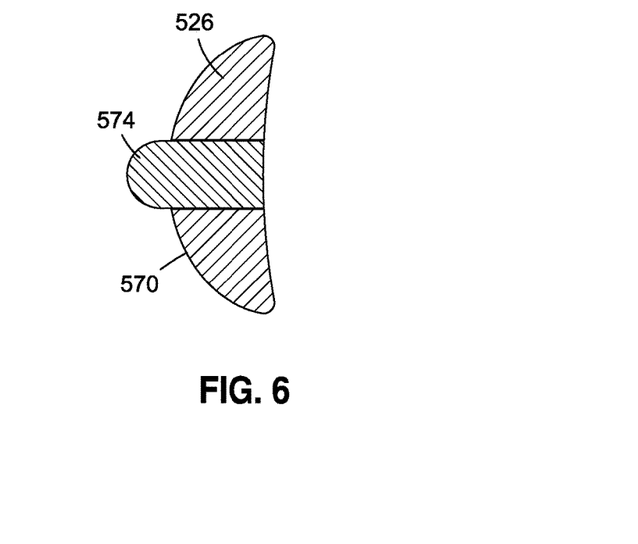
FIG. 6 shows a cross section of the handle of the embodiment of FIG. 5.
Figure 7:
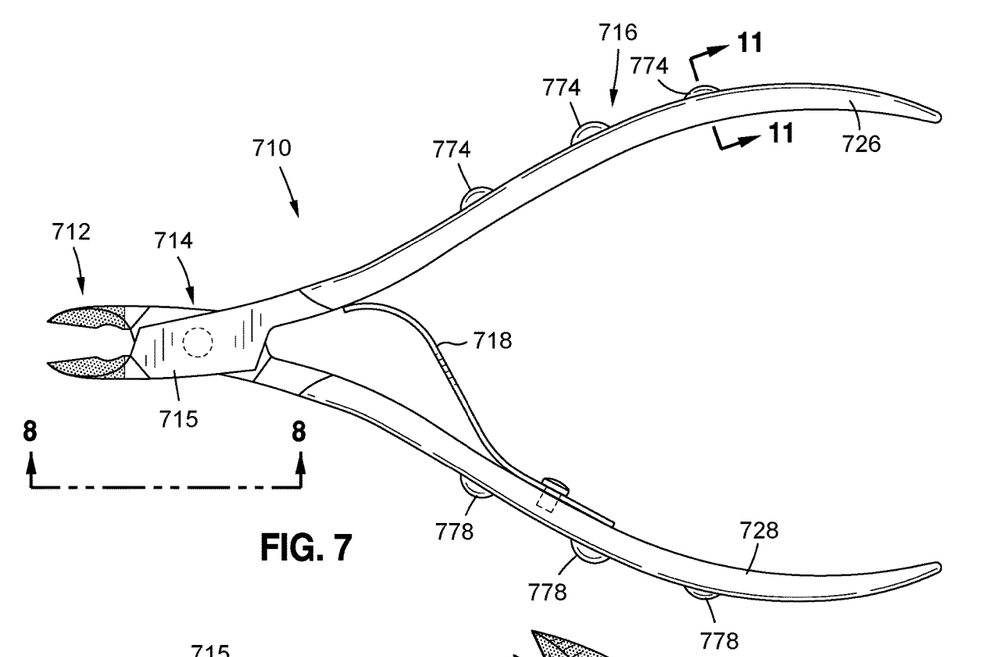
FIG. 7 shows a top view of yet another embodiment of the nipper device.
Figure 8:
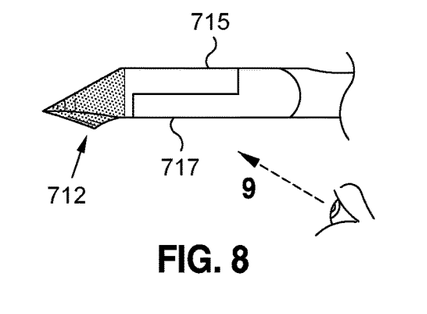
FIG. 8 shows a side view of an end portion of the nipper device depicted in FIG. 7.
Figure 9:
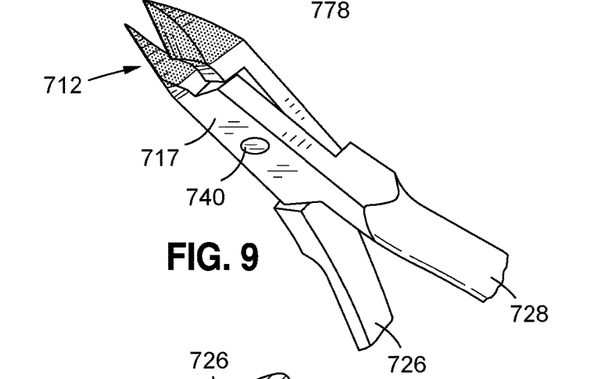
FIG. 9 shows a lower perspective view of the end portion of the nipper device depicted in FIG. 8.
Figure 10:
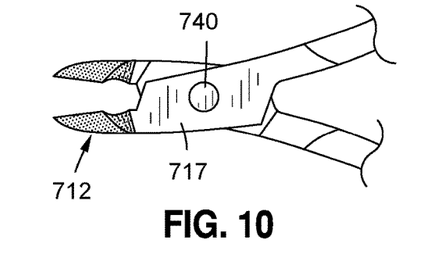
FIG. 10 shows a bottom view of the end portion of the nipper device depicted in FIG. 8.

FIG. 6 shows a cross section of the first handle 526 of the embodiment of FIG. 5, taken along a plane indicated by the line 6-6 in FIG. 5. The magnetized slug 574 in FIG. 6 is recess mounted, with the recess extending completely through the cross section of the handle 526. In other embodiments, the recess may extend only partially through the handle. Varying the depth of the recess allows for varying the size of the magnetized slugs used in the device, or the same size slugs may be used in combination with recesses of varying depth to cause one or more of the magnetized slugs to extend different distances beyond the exterior surface of the handle. In combination with the spacing of the slugs in the first handle 526 and second handle 528, varying the size of the magnetized slug allows for the optimization of the size and shape of the magnetic field.

As noted above, the shape, specifically the length, of the magnetized slug itself may also vary. In some embodiments, all the slugs are of a uniform length, and thus, in combination with recesses of equivalent depth or surface mounting, extend from the handle a uniform distance. In other embodiments, each magnetized slug may be of a different length, extending from the handle a different amount. In still other embodiments, some of the magnetized slugs may be of the same length, and others may be of varying lengths. The length of the portion of the magnetic slug extending form the exterior surface of the handle affects the ease of griping the handle, by preventing the slippage of the fingers or thumb of a user forward or backward along the first handle or second handle.

Referring now to FIGS. 7-10, there is depicted yet another embodiment of a nipper device 710. The general structure of the nipper device 710 is similar to that shown in FIG. 5, with the primary distinction being the size of the magnets, as will be described in more detail below.

The nipper device 710 generally includes a jaw 712, a pivot section 714, and a handle section 716 including a first handle 726 and a second handle 728. Spring 718 is operatively coupled to the handles 726, 728 and provides the biasing force thereto, as discussed above. A first set of magnets 774 is coupled to the first handle 726 and a second set of magnets 778 is coupled to the second handle 728. The sizes of the magnets in each set of magnets 774, 778 may vary. For instance, each set of magnets 774, 778 may include a small magnet, an intermediate magnet, and a large magnet. Furthermore, the magnets 774, 778 may be mounted to the respective handle 726, 728 in a manner wherein the distance by which each magnet 774, 778 protrudes beyond the outer surface of the respective handle 726, 728 may vary. In other words, some magnets 774, 778 may protrude from the corresponding handle 726, 728 more than others. The difference in size and projection of the magnets 774, 778 may enhance the massaging effect provided by the magnets 774, 778, as well as mitigating slippage of the individual gripping the nipper device 710.

Figure 11:
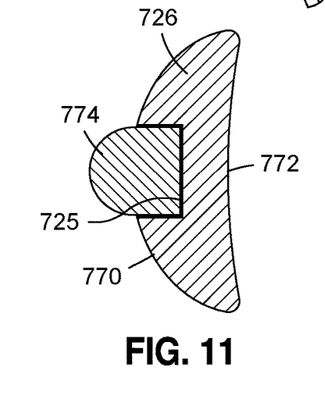
FIG. 11 shows a cross sectional view of a handle arm having a magnetic element coupled thereto.

According to one embodiment, each handle 726, 728 includes a plurality of recesses formed therein, with each recess being configured to receive a single magnet. Each recess extends from an outer surface of the handle toward an opposing inner surface, with the recess terminating before reaching the inner surface. In this regard, each recess extends only partially through the corresponding handle. In the example depicted in FIG. 11, recess 725 extends partially through the handle 726 from outer surface 770 toward the inner surface 772.

The pivot section 714 of the nipper device 710 includes opposing outer surfaces 715, 717 which are generally planar, and parallel to each other. Surface 715 is integrally formed with the first handle 726, while surface 717 is integrally formed with the second handle 728. The pivot section may additionally include pivot pin 740, which may extend within a bore formed within the pivot section 714. The bore may extend between the outer surfaces 715, 717. In the exemplary embodiment, the bore extends only partially between the outer surfaces 715, 717, with the bore extending from outer surface 717 and terminating before reaching outer surface 715. In this regard, the pivot pin 740 may be concealed from one side of the nipper device 710.

The above description is given by way of example, and not limitation. Given the above disclosure, one skilled in the art could devise variations that are within the scope and spirit of the present disclosure, including various shapes and sizes of the first blade and second blade. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:
1. A nipper comprising:
 a jaw including a first blade and a second blade pivotable relative to the first blade, the jaw being formed from a carbide material;

a handle coupled to the jaw, the handle including a first arm coupled to the first blade and a second arm coupled to the second blade, the first arm being pivotable relative to the second arm; and at least one first magnet having a first portion extending into the first arm and a second portion defining an exposed, convex surface protruding from the first arm a first distance from an outer surface of the first arm;

at least one second magnet having a first portion extending into the first arm and a second portion protruding from the first arm a second distance from the outer surface of the first arm;

the jaw and the handle being configured such that pivotable movement of the first arm relative to the second arm causes pivotal movement of the first blade relative to the second blade.

2. The nipper recited in claim 1, wherein the at least one first magnet includes a plurality of first magnets coupled to the first arm.

3. The nipper recited in claim 2, wherein the first arm includes a plurality of recesses formed therein, the plurality of first magnets being located in respective ones of the plurality of recesses.

4. The nipper recited in claim 1, further comprising at least one second magnet coupled to the second arm.

5. The nipper recited in claim 1, further comprising a spring operatively engaged to the first arm and the second arm, the spring being adapted to impart a biasing force on the first arm and the second arm and to urge the first arm and the second arm to pivot away from each other.

6. The nipper recited in claim 1, further comprising a pivot pin coupled to the first arm and the second arm, the first arm and the second arm being pivotable about the pivot pin.

7. The nipper recited in claim 1, wherein the first blade and the second blade include respective linear blade edges.

8. The nipper recited in claim 1 further comprises a biasing member operatively engaged between the first and second arms to bias the first and second arms away from each other.

9. The nipper recited in claim 1, wherein the second portion of the at least one first magnet is configured to interface directly with a user.

10. A nipper comprising:
a cutting portion including a first cutting edge and a second cutting edge, the first and second cutting edges being pivotable relative to each other to effectuate cutting of an object;
a handle portion coupled to the cutting portion, the handle portion including a pair of handle arms each having a handle surface, at least a portion of the handle surface having a curved surface, the pair of handle arms being pivotable relative to each other; and
a plurality of magnetized massaging elements each protruding from a respective handle surface of a respective one of the handle arms and defining an exposed, convex surface, the elements configured to emit a magnetic field and being configured to provide a massaging effect on a user gripping the handle portion.

11. The nipper recited in claim 10, wherein the first cutting edge and the second cutting edge are formed of a carbide material, the first cutting edge and the second cutting edge being brazed to the handle portion, the handle portion being formed from a non-carbide material.

12. The nipper recited in claim 10, wherein the first cutting edge and the second cutting edge are linear.

13. The nipper recited in claim 10, wherein each handle arm includes a plurality of recesses formed therein, each massaging element being received in a respective one of the plurality of recesses.

14. The nipper recited in claim 10, further comprising a spring operatively engaged to the pair of handle arms, the spring being adapted to impart a biasing force on the pair of handle arms and to urge the pair of handle arms to pivot away from each other.

15. The nipper recited in claim 10, further comprising a pivot pin coupled to the pair of handle arms, the pair of handle arms being pivotable about the pivot pin.

16. The nipper recited in claim 10 further comprises a biasing member operatively engaged between the pair of handle arms to bias the pair of handle arms away from each other.

17. The nipper device recited in claim 10 wherein at least two of the magnetized massaging elements protrude different distances from the handle surface.

18. A method of forming a nipper, the method comprising the steps of:
forming a pair of nipper arms, each nipper arm having a cutting portion and a handle portion each handle portion having a curved outer surface, the cutting portion being at least partially comprised of a carbide material;
forming a plurality recesses in each of the pair of nipper arms;
at least partially magnetizing the handle portion of each nipper arm by connecting a plurality of magnets each defining an exposed, convex surface to a respective handle portion by placing magnets into the plurality of recesses such that the plurality of magnets define at least a portion of the curved outer surface of the handle portion; and
connecting the pair of nipper arms such that the pair of nipper arms are pivotally connected to each other.

19. The method recited in claim 18, wherein the step of forming a pair of nipper arms includes brazing each nipper arm to join the carbide material to the corresponding handle portion.

20. The method recited in claim 18, wherein the step of connecting the pair of nipper arms includes connecting the pair of nipper arms via a pivot pin.

21. The method recited in claim 18 wherein the plurality of magnets are placed into the recesses such that at least two of the plurality of magnets protrude at different distances from the curved outer surface of the handle portion.

* * * * *